Figure 1:
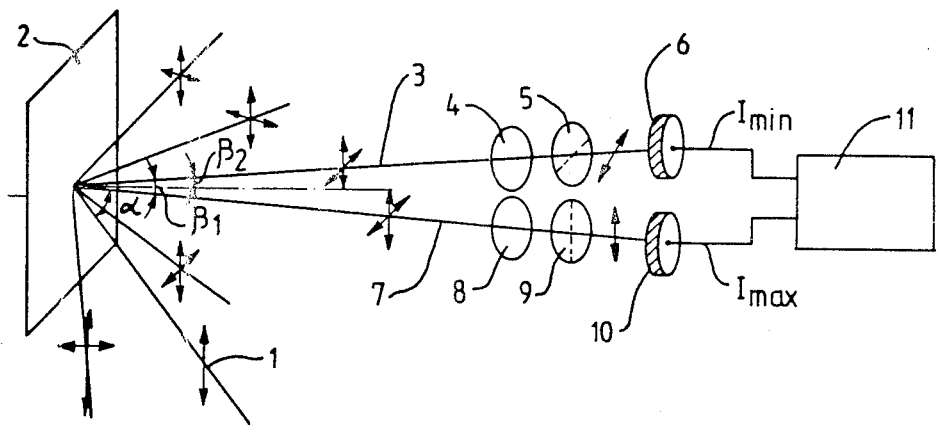

United States Patent [19]

Hirvonen

[11] Patent Number: 4,764,017

[45] Date of Patent: Aug. 16, 1988

[54] METHOD FOR IDENTIFYING TIMBER SURFACE PROPERTIES

[75] Inventor: Kullervo Hirvonen, Varkaus, Finland

[73] Assignee: Altim Control OY, Varkaus, Finland

[21] Appl. No.: 4,635

[22] Filed: Jan. 20, 1987

[30] Foreign Application Priority Data

Jan. 21, 1986 [FI] Finland .................................. 860245

[51] Int. Cl.⁴ ..................... G01N 21/21; G01N 21/27
[52] U.S. Cl. ..................................... 356/369; 356/237
[58] Field of Search ............... 356/237, 366, 367, 369; 250/225

[56] References Cited

U.S. PATENT DOCUMENTS 3,694,658  9/1972  Watson et al. .................. 356/237 X
3,976,384  8/1976  Matthews et al. .............. 356/237 X
4,482,250 11/1984  Hirvonen et al. .
4,525,850  3/1986  Wang et al. ....................... 372/68 X Primary Examiner—Davis L. Willis
Assistant Examiner—Matthew W. Koren
Attorney, Agent, or Firm—Nixon & Vanderhye

[57] ABSTRACT

A method for identifying timber surface properties using linearly polarized electromagnetic radiation containing various different wavelength components. Of the scattered radiation are measured by wavelength ranges the intensity components $I_{min}$ and $I_{max}$ that are mutually perpendicular as regards their polarization plane, wherein the polarization plane of the component $I_{max}$ is the same as that of the radiation directed to the surface. The identification of the surface types is made on the basis of the information about the color tone of the surface and the fiber structure achieved from the variables $I_{min}$ and $P=(I_{max}-I_{min})/(I_{max}+I_{min})$.

14 Claims, 2 Drawing Sheets

METHOD FOR IDENTIFYING TIMBER SURFACE PROPERTIES

The present invention relates to a method for identifying the surface properties of timber, of sawn and planed timber and plywood in particular, when automatically determining defects and quality.

Sawn timber and plywood products to be used for various purposes are classified according to the surface properties of the product. The most important factors affecting the quality (and the strength) are knots, rot, bluestain, rough edges, skewness of grains, grub passages and mechanical defects. The price of board and plywood products is determined by quality classification.

The methods used today for determining timber surface properties or defects are based on tracing the intensity plane of radiation scattered from or gone through the surface to which electromagnetical radiation is directed by means of special geometrical arrangements. Depending on the radiation source, various light and radiation detectors as well as video and diode matrice cameras have been used for the detection. When cameras are used, image processing and pattern recognition algorithms setting great demands on computer capacity are often resorted to. In order to trace different defects, several wavelengths as well as different wavelength filters have been used in connection with the detectors and the cameras.

Specially suitable radiation sources for examining surfaces are lasers which yield a strong, monochromatic, collimated, coherent and often linearly polarized beam of light. It is easy to deviate a laser beam so that the entire surface to be examined can be analysed. A laser beam can also be focused into a very small spot, which enables also the examining of small surface parts having a size of about a micrometer.

The present invention improves the method disclosed in the U.S. Pat. No. 4,482,250. In the method of said patent the timber surface is scanned with a linearly polarized light beam the polarization plane of which is fixed according to the timber surface, and from the radiation reflected from the surface is measured the intensity component $I_{max}$ that has maintained the polarization plane and the intensity component $I_{min}$ that is perpendicular to it, and a depolarization variable is formed:

$$P = \frac{I_{max} - I_{min}}{I_{max} - I_{min}}$$

The variable $I_{min}$ discloses darkness variations of the surface and the variable P discloses the fiber structure. By means of these variables a very far going identification of defects can be performed without a large computer capacity.

Behaviour of the variables $I_{min}$ and P depends on the used wavelength or wavelength range. An especially suitable wavelength for the inspection of a timber surface is 632,8 nm of a helium-neon laser, with which a darkness contrast in relation to a healthy surface can be achieved for all central defect types on timber surface.

The method according to the present invention improves the ability of the above mentioned method to separate defects between themselves by means of observing the behaviour of the variable $I_{min}$ while using two or several wavelengths or wavelength ranges and at the same time the behaviour of the variable P while using one or several wavelengths or wavelength ranges. When moving within the wavelength range of e.g. visible light information is received of intensity signals connected to the colour tone of the timber surface instead of contrast information of one wavelength. Accordingly different types of defects having possibly the same darkness contrast and fiber structure value can be identified on the basis of the colour tone. This feature can be used in identifying especially the following defects: rot, bluestain, colour defect and dirt.

Figure 2:
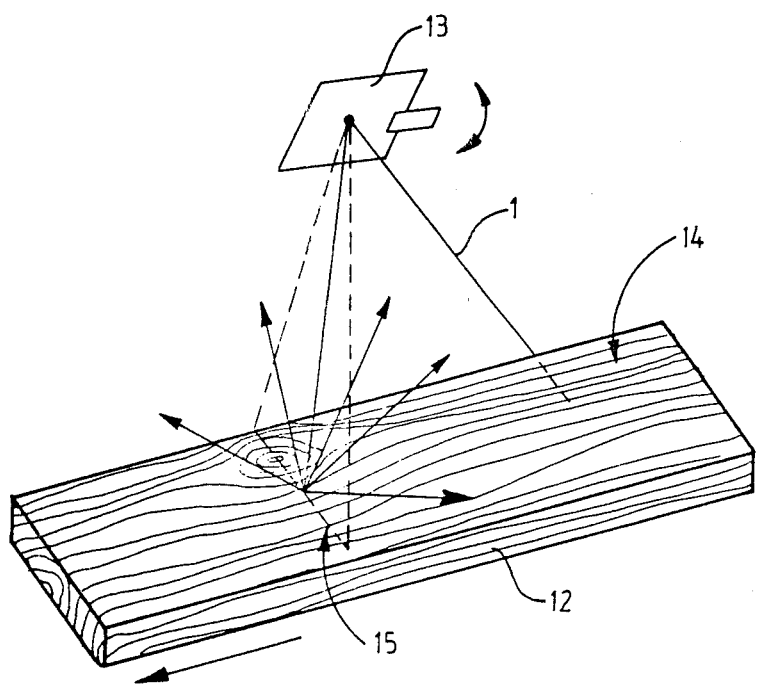
Figure 3:
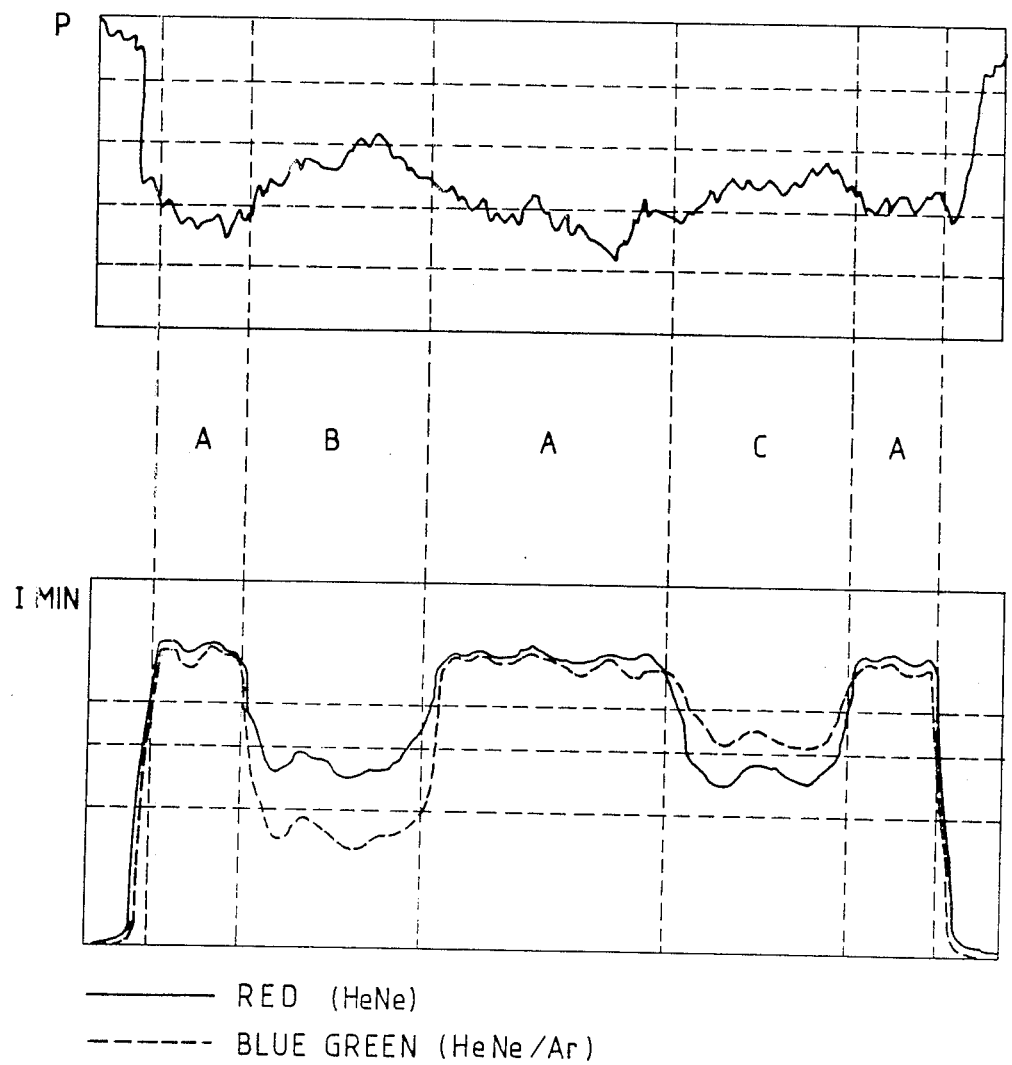

The invention is described in more detail in the following with reference to the accompanying drawings, in which FIG. 1 shows the principle of the equipment for one wavelength/wavelength range used in carrying out the method according to the invention, FIG. 2 shows a simplified diagram illustrating the examining of the surface of sawn timber, and FIG. 3 shows the use of information about the colour tone in the identification of different types of defects (rot and bluestain) when using two wavelengths.

In the measurement device shown in FIG. 1, reference number 1 refers to a light beam projected from a laser and directed towards the surface 2 of the object to be examined. The direction of the incident beam and the direction perpendicular to the surface form an angle α, which is preferably smaller than 30°. Part 3 of the diffused scattered radiation passes through a filter 4 corresponding to the used wavelength (interference) and through a polarization filter 5 to a detector 6 and part 7 (interference) through a filter 8 and a polarization filter 9 to a detector 10. The measuring directions of the scattered radiation and the direction perpendicular to the surface form angles $\beta_1$ and $\beta_2$, which are preferably smaller than 30°. The transmission directions of the polarizing filters are at an angle of 90° and the directions are defined by turning the filter 9 so that the intensity signal given by the detector 10 is at its largest ($I_{max}$) and correspondingly the value of the detector 6 at its lowest ($I_{min}$). The polarization of $I_{max}$ is the same as the polarization plane of the incident light if the length direction of the fibers of the timber surface is the same as the growth direction of the wood, as is normally the case. The intensity signals $I_{max}$ and $I_{min}$ are transmitted to a processor 11 where they are, in a manner known per se, transformed to a form suitable for determining the quality of timber.

The principal arrangement of the equipment intended for examining a board 12 is shown in FIG. 2. The light beam 1 is by means of a swivelling deviation mirror 13 caused to scan over a timber surface 14 in the cross direction of the board along a course 15. The board is moved in the longitudinal direction. The radiation scattered from the board surface is detected by the means according to FIG. 1. The light beam 1 includes two or several wavelength components.

FIG. 3 discloses a typical behaviour of intensity signals that are standardized as regards their level and received during a single light beam scan on a healthy (A), rotten (B) and bluestained (C) timber surface when the red wavelength of a HeNe-laser and one wavelength of a blue green laser (e.g. ARGON or HeNe) are used. The figure also illustrates how the knowledge about the colour tone can be used to separate between themselves rot and bluestain in the present case, although the depolarization (P) is the same for said surface types.

The invention is not limited to the above embodiment but it can be modified and applied within the inventive concept defined by the claims.

I claim:

1. A method for determining timber surface characteristics comprising the steps of:
   directing electromagnetic radiation of at least two different wavelengths to the surface to be examined such that each wavelength component is linearly polarized with the polarization plane parallel or perpendicular to the normal growth direction of the wood fibers of the surface to be examined;
   measuring separately for each wavelength component the intensity components $I_{min}$ and $I_{max}$ of the scattered radiation, the intensity components $I_{min}$ and $I_{max}$ having polarization planes of scattered radiation perpendicular to one another with the polarization plane of the component $I_{max}$ being the same as the polarization plane of the incident radiation;
   determining the degree of depolarization for one of said wavelength components by using $P=(I_{max}-I_{min})/(I_{max}+I_{min})$; and
   determining timber surface characteristics using information about the color tones of the variables $I_{min}$ and the degree of depolarization P for one wavelength component.

2. A method according to claim 1 wherein the step of directing electromagnetic radiation includes the step of scanning the timber surface with the red wavelength of a HeNe laser and one wavelength of a blue-green laser.

3. A method according to claim 2 wherein the blue-green laser is a HeNe laser.

4. A method according to claim 2 wherein the blue-green laser is an argon laser.

5. A method according to claim 1 wherein the step of determining the timber surface characteristics includes using the color tones to distinguish rot and bluestain in the timber surface.

6. A method according to claim 1 wherein the step of determining timber surface characteristics includes using information about the degree of depolarization P for more than one wavelength component.

7. Apparatus for determining timber surface characteristics comprising:
   means for directing electromagnetic radiation of at least two different wavelengths to the surface to be examined such that each wavelength component is linearly polarized with the polarization plane parallel or perpendicular to the normal growth direction of the wood fibers of the surface to be examined;
   means for measuring separately for each wavelength component the intensity component $I_{min}$ and $I_{max}$ of the scattered radiation, the intensity components $I_{min}$ and $I_{max}$ having polarization planes of scattered radiation perpendicular to one another with the polarization plane of the component $I_{max}$ being the same as the polarization plane of the incident radiation;
   means for determining the degree of polarization for one of said wavelength components by using $P=(I_{max}-I_{min})/(I_{max}+I_{min})$; and
   means for determining timber surface characteristics using information about the color tones of the components $I_{min}$ and the degree of polarization P for one wavelength component.

8. Apparatus according to claim 7 including means for scanning the timber surface with the red wavelength of a HeNe laser and one wavelength of a blue-green laser.

9. Apparatus according to claim 8 wherein the blue-green laser is a HeNe laser.

10. Apparatus according to claim 8 wherein the blue-green laser is an argon laser.

11. Apparatus according to claim 7 including means for using information about the degree of depolarization P for more than one wavelength component.

12. Apparatus according to claim 7 including means for scanning the timber surface with the red wavelength of a HeNe laser and one wavelength of a blue-green laser.

13. Apparatus according to claim 12 wherein the blue-green laser is a HeNe laser.

14. Apparatus according to claim 12 wherein the blue-green laser is an argon laser.

* * * * *